United States Patent
Yokoyama et al.

(10) Patent No.: US 9,518,944 B2
(45) Date of Patent: Dec. 13, 2016

(54) TEMPERATURE-CONTROLLED BATH

(71) Applicant: MITUTOYO CORPORATION, Kanagawa (JP)

(72) Inventors: Yuichiro Yokoyama, Ibaraki (JP); Takeshi Hagino, Ibaraki (JP)

(73) Assignee: MITUTOYO CORPORATION, Kanagawa (JP)

( * ) Notice: Subject to any disclaimer, the term of this patent is extended or adjusted under 35 U.S.C. 154(b) by 437 days.

(21) Appl. No.: 14/295,781

(22) Filed: Jun. 4, 2014

(65) Prior Publication Data
US 2015/0003494 A1 Jan. 1, 2015

(30) Foreign Application Priority Data

Jun. 27, 2013 (JP) .................. 2013-134473

(51) Int. Cl.
*G01N 25/16* (2006.01)
*G01N 1/44* (2006.01)

(52) U.S. Cl.
CPC ............... *G01N 25/16* (2013.01); *G01N 1/44* (2013.01)

(58) Field of Classification Search
CPC ...................................... G01N 25/16
See application file for complete search history.

(56) References Cited

U.S. PATENT DOCUMENTS

| | | | | |
|---|---|---|---|---|
| 2,351,572 A * | 6/1944 | Kingston | ............... | G01N 25/16 374/55 |
| 4,456,389 A * | 6/1984 | Regenass | ............... | G01K 17/04 374/31 |
| 4,599,169 A * | 7/1986 | Ray | ........................ | G01N 30/30 210/175 |
| 5,508,197 A * | 4/1996 | Hansen | ..................... | B01L 7/52 422/109 |
| 5,807,426 A * | 9/1998 | Ohtsuki | ................. | G01N 30/30 73/23.25 |
| 7,104,680 B2 * | 9/2006 | Nakamura | ............... | G01N 5/04 374/45 |
| 2009/0226903 A1 * | 9/2009 | Cobb | .................. | B01L 3/50851 435/6.11 |

FOREIGN PATENT DOCUMENTS

JP 02253146 A * 10/1990
JP 2004-226369 8/2004

* cited by examiner

*Primary Examiner* — Minh Phan
*Assistant Examiner* — Leon W Rhodes, Jr.
(74) *Attorney, Agent, or Firm* — Greenblum & Bernstein, P.L.C.

(57) ABSTRACT

A temperature-controlled bath capable of swiftly changing the temperature of a sample to a target temperature and maintaining the temperature of the sample at a fixed temperature after the temperature change is provided. A temperature-controlled bath includes a temperature changing means, a temperature-controlled chamber, a sample holding chamber, and connection cut-off means. The temperature changing means is disposed in the temperature-controlled chamber, and the temperature of the temperature-controlled chamber is adjusted by the temperature changing means. The sample holding chamber is separated from the temperature-controlled chamber by a thermally conducive wall, and contains a sample therein. The connection cut-off means change a connection between the temperature-controlled chamber and the sample holding chamber to a connected state or a cut-off state.

12 Claims, 12 Drawing Sheets

TEMPERATURE-CONTROLLED BATH

INCORPORATION BY REFERENCE

This application is based upon and claims the benefit of priority from Japanese patent application No. 2013-134473, filed on Jun. 27, 2013, the disclosure of which is incorporated herein in its entirety by reference:

BACKGROUND OF THE INVENTION

1. Field of the Invention

The present invention relates to a temperature-controlled bath.

2. Description of Related Art

Temperature-controlled baths that change the temperatures of samples to target temperatures have been used.

For example, Japanese Unexamined Patent Application Publication No. 2004-226369 discloses a temperature-controlled bath including temperature control means for sending air at a preset temperature and a fan that stirs the air and thereby prevents stagnant air. This temperature-controlled bath can swiftly change the temperature of a sample to a target temperature. By using such a temperature-controlled bath, it is possible to measure the length of a sample at each temperature and thereby to obtain the coefficient of linear expansion of the sample.

SUMMARY OF THE INVENTION

The present inventors have found following problems. That is, in the temperature-controlled bath disclosed in Japanese Unexamined Patent Application Publication No. 2004-226369, the temperature of the sample could fluctuate from the target temperature after the sample temperature is changed to the target temperature. More specifically, in order to maintain the temperature inside the temperature-controlled bath at the target temperature, the temperature control means sends air whose temperature is changed so that a deviation from the target temperature is cancelled out. When this sent air comes into contact with the sample, the temperature of the sample could fluctuate from the target temperature. Therefore, it has been desired to develop a temperature-controlled bath capable of swiftly changing the temperature of a sample to a target temperature and maintaining the temperature of the sample at a fixed temperature after the temperature change.

The present invention has been made in view of the above-described situation, and an object thereof is to provide a temperature-controlled bath capable of swiftly changing the temperature of a sample to a target temperature and maintaining the temperature of the sample at a fixed temperature after the temperature change.

A first exemplary aspect of the present invention is a temperature-controlled bath including: temperature changing means for heating or cooling a gas so that the temperature of the gas is adjusted to a set temperature; a temperature-controlled chamber whose temperature is adjusted by the temperature changing means, the temperature changing means being disposed in the temperature-controlled chamber; a sample holding chamber containing a sample therein, the sample holding chamber being separated from the temperature-controlled chamber by a thermally conducive wall; and connection cut-off means for changing a connection between the temperature-controlled chamber and the sample holding chamber to a connected state or a cut-off state.

According to this configuration, it is possible to swiftly change the temperature of a sample to a target temperature and maintain the temperature of the sample at a fixed temperature after the temperature change.

Further, the above-described temperature-controlled bath may further include first blower means for sending a gas whose temperature is adjusted by the temperature changing means mainly into the temperature-controlled chamber. Further, the above-described temperature-controlled bath may further include: an air hole that serves as an inlet/outlet of the gas between the temperature-controlled chamber and the sample holding chamber; second blower means for sending the gas in the temperature-controlled chamber into the sample holding chamber through the air hole; and third blower means for sending out the gas in the sample holding chamber toward the temperature-controlled chamber through the air hole. Further, in the above-described temperature-controlled bath, the thermally conducive wall may include at least one of a radiator plate protruding toward the temperature-controlled chamber and a radiator plate protruding toward the sample holding chamber. In the above-described temperature-controlled bath, the sample holding chamber may include a probe inserting hole for inserting a probe into the sample holding chamber, the probe inserting hole being able to be opened and closed. Further, in the above-described temperature-controlled bath, the sample holding chamber may include an optically transparent window for enabling optical measurement of the sample. Further, in the above-described temperature-controlled bath, the connection cut-off means may be an open/close shutter that opens/closes by rotating a plate member, and the plate member may be an air-permeable plate member capable of letting a gas pass through the plate member.

Another exemplary aspect of the present invention is a linear expansion coefficient measuring device including: the above-described temperature-controlled bath; measurement means for measuring a length of the sample at different temperatures; and calculation means for calculating a coefficient of linear expansion of the sample based on the length of the sample at each temperature.

According to this configuration, it is possible to measure the coefficient of linear expansion of the sample at each temperature.

Another exemplary aspect of the present invention is a temperature control method for a temperature-controlled bath, the temperature-controlled bath including: temperature changing means for heating or cooling a gas so that the temperature of the gas is adjusted to a set temperature; a temperature-controlled chamber whose temperature is adjusted by the temperature changing means, the temperature changing means being disposed in the temperature-controlled chamber; a sample holding chamber containing a sample therein, the sample holding chamber being separated from the temperature-controlled chamber by a thermally conducive wall; and connection cut-off means for changing a connection between the temperature-controlled chamber and the sample holding chamber to a connected state or a cut-off state, the temperature control method including: bringing an air hole into a connected state when a temperature of the sample is to be changed, the air hole serving as an inlet/outlet of the gas between the temperature-controlled chamber and the sample holding chamber; and bringing the air hole into a cut-off state when the temperature of the sample is to be maintained at a fixed temperature.

According to this configuration, it is possible to swiftly change the temperature of a sample to a target temperature and maintain the temperature of the sample at a fixed temperature after the temperature change.

According to the present invention, it is possible to provide a temperature-controlled bath capable of swiftly changing the temperature of a sample to a target temperature and maintaining the temperature of the sample at a fixed temperature after the temperature change.

The above and other objects, features and advantages of the present invention will become more fully understood from the detailed description given hereinbelow and the accompanying drawings which are given by way of illustration only, and thus are not to be considered as limiting the present invention.

DESCRIPTION OF THE EXEMPLARY EMBODIMENTS

First Exemplary Embodiment

Figure 1:
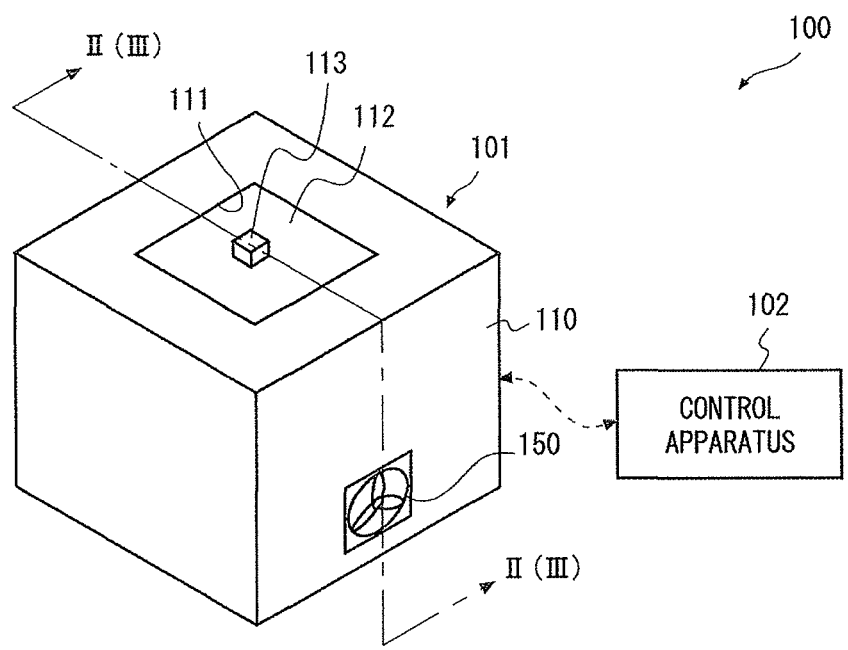
FIG. 1 shows a temperature-controlled bath system according to a first exemplary embodiment.
Figure 2:
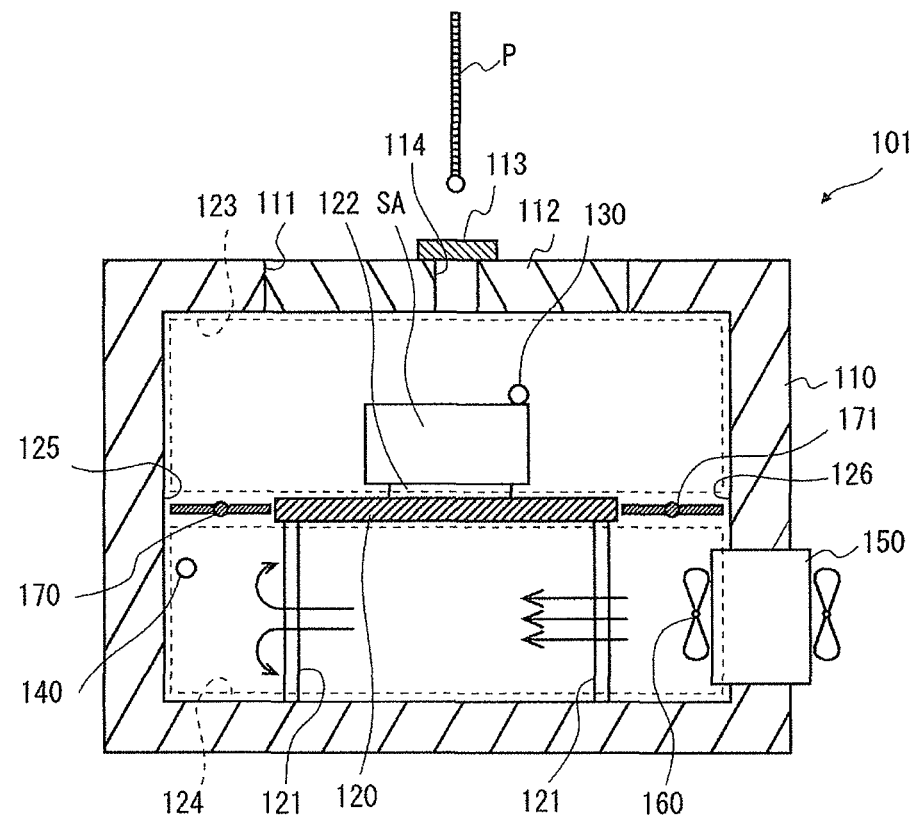
FIG. 2 is a cross section of a temperature-controlled bath according to the first exemplary embodiment.
Figure 3:
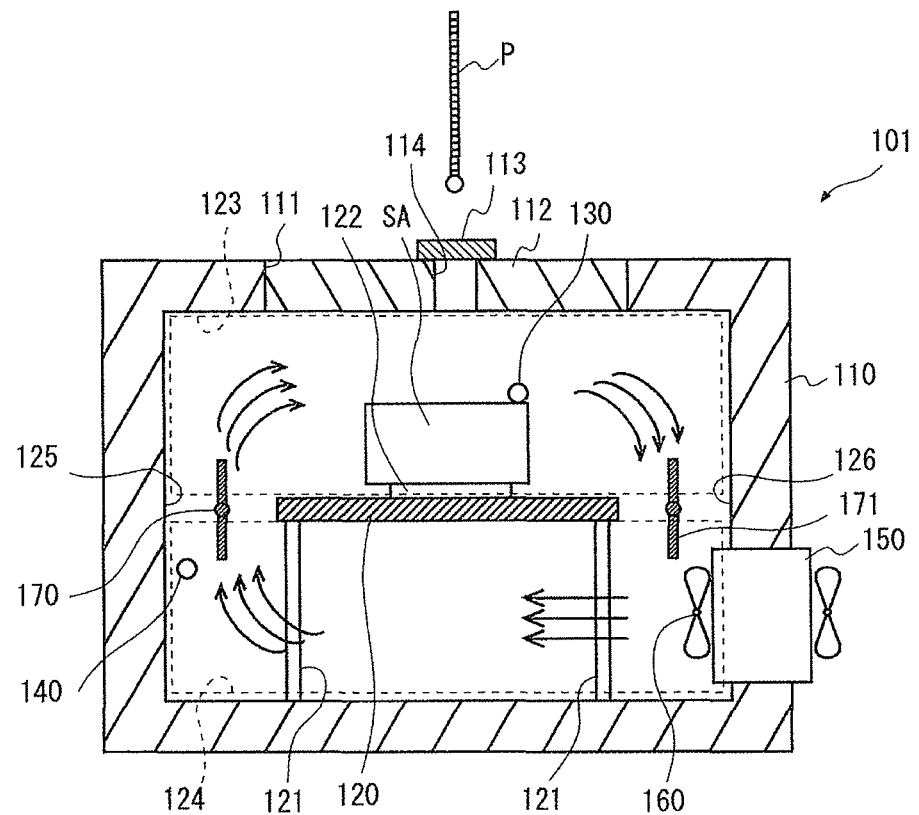
FIG. 3 is a cross section of a temperature-controlled bath according to the first exemplary embodiment.
Figure 4:
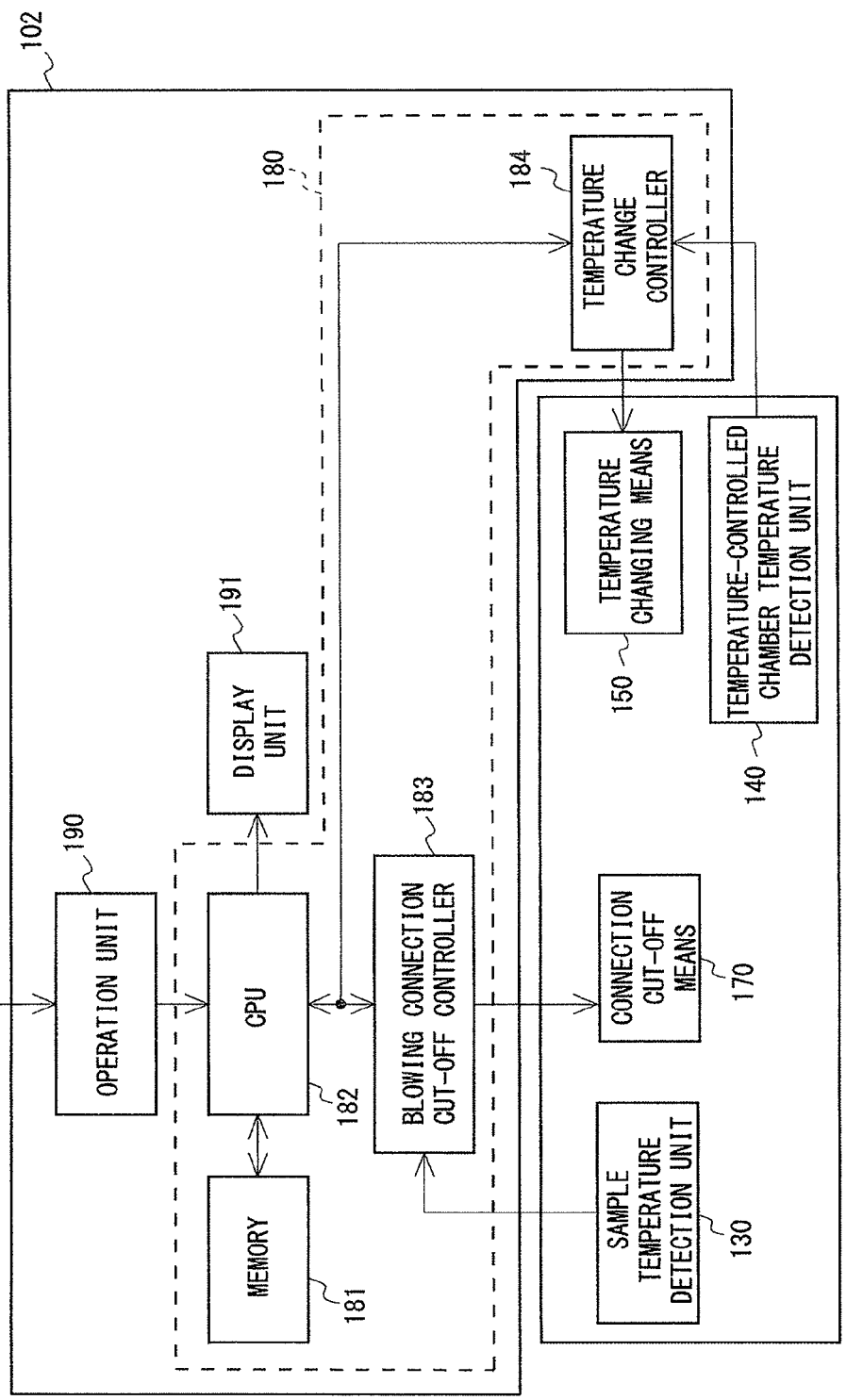
FIG. 4 is a block diagram of a temperature-controlled bath system according to the first exemplary embodiment.

A temperature-controlled bath system according to a first exemplary embodiment is explained with reference to FIGS. 1 to 4. FIG. 1 shows a temperature-controlled bath system according to the first exemplary embodiment. FIGS. 2 and 3 are cross sections of the temperature-controlled bath according to the first exemplary embodiment. FIG. 4 is a block diagram of the temperature-controlled bath system according to the first exemplary embodiment.

As shown in FIG. 1, a temperature-controlled bath system 100 includes a temperature-controlled bath 101 and a control apparatus 102. The temperature-controlled bath system 100 is disposed inside a linear expansion coefficient measuring device equipped with a probe P, and used in that state. The linear expansion coefficient measuring device (which is also referred to as "calculation means") can measure the length of a sample SA at a plurality of temperatures by using the probe P (which is also referred to as "measurement means") and calculate the coefficient of linear expansion of the sample SA based on this measurement result.

As shown in FIGS. 2 and 3, the temperature-controlled bath 101 includes a housing 110, a sample holding plate 120, a sample temperature measurement unit 130, a temperature-controlled chamber temperature measurement unit 140, temperature changing means 150, blower means 160 (which is also referred to as "first blower means"), and connection cut-off means 170 and 171.

As shown in FIGS. 1 and 2, the housing 110 is, for example, a roughly rectangular parallelepiped housing made of insulating material. The housing 110 has a sample introducing opening 111, which is provided to place the sample SA inside the housing 110, on its upper surface. The sample introducing opening 111 is hermetically closed by a sample introducing opening lid 112. The shape and size of the housing 110 may be changed as desired according to the shape and size of the sample SA and/or the blowing ability of the blower means 160. The sample introducing opening lid 112 includes a probe inserting opening 114 for inserting the probe P into the housing 110 and a probe inserting opening lid 113 for closing the probe inserting opening 114.

The sample holding plate 120 is supported by supporting legs 121 and disposed so as to divide the internal space of the housing 110 into two sections, i.e., upper and lower sections. The sample holding plate 120 holds the sample SA with a sample holding pedestal 122 interposed therebetween. As described above, the internal space of the housing 110 is divided into two sections by the sample holding plate 120. However, there are two gaps between the housing 110 and the sample holding plate 120. These gaps are referred to as "first vent 125" (which is also referred to as "air hole") and "second vent 126" (which is also referred to as "air hole") respectively. Of these two internal space sections of the housing 110, the upper space serves as a sample holding chamber 123 and the lower space serves as a temperature-controlled chamber 124. The sample holding chamber 123 contains the sample SA therein. The sample holding plate 120 is made of thermally conductive material having a high thermal conductivity. The sample holding plate 120 serves as a thermally conductive wall and separates the sample holding chamber 123 from the temperature-controlled chamber 124. Examples of such thermally conductive material include copper and copper alloys. The sample holding plate 120 preferably has a predetermined wall thickness so that the sample holding plate 120 slowly conducts heat from the temperature-controlled chamber 124 to the sample SA. Further, the sample holding plate 120 may include at least one of a radiator plate protruding toward the temperature-controlled chamber 124 and a radiator plate protruding toward the sample holding chamber 123.

The sample temperature measurement unit 130 is disposed in close-contact (or direct-contact) with the sample SA and measures the temperature of the sample SA (hereinafter called "sample temperature"). The sample temperature measurement unit 130 generates a signal indicating the sample temperature.

The temperature-controlled chamber temperature measurement unit 140 is disposed in the temperature-controlled chamber 124 and measures the temperature of the temperature-controlled chamber 124 (hereinafter called "temperature-controlled chamber temperature"). The temperature-controlled chamber temperature measurement unit 140 generates a signal indicating the temperature-controlled chamber temperature.

The temperature changing means 150 is disposed in the housing 110 in such a manner that the temperature changing means 150 is embedded in the wall that separates the temperature-controlled chamber 124 from the outside (i.e., from the lower space). The temperature changing means 150 is disposed closer to the first vent 125 than to the second vent 126. The temperature changing means 150 mainly changes the temperature of the temperature-controlled chamber 124 rather than the temperature of the sample holding chamber 123. A heat exchanger, for example, can be used for the temperature changing means 150. The temperature changing means 150 receives a control signal and heats or cools the gas in the temperature-controlled chamber 124 in response to the control signal, and thereby changes the temperature of the gas in the temperature-controlled chamber 124 to a predetermined temperature. Examples of the gas include atmospheric air.

The blower means 160 is disposed in the vicinity of the temperature changing means 150 and can send the gas, whose temperature has been changed by the temperature changing means 150. The blower means 160 has at least a sufficient blowing ability to circulate the gas inside the housing 110. The blowing direction of the blower means 160 is a direction toward the temperature-controlled chamber 124 (i.e., the lower space). To come into contact with the sample SA, the gas sent from the blower means 160 mainly passes through the first vent 125, which is the vent further from the blower means 160. The blower means 160 operates as a slave component of the temperature changing means 150. For example, a built-in fan of a heat exchanger, which serves as the temperature changing means 150, may be used as the blower means 160.

The connection cut-off means 170 and 171 are disposed between the sample holding plate 120 and the housing 110, and can cut off the sample holding chamber 123 from the temperature-controlled chamber 124 (see FIG. 2) or connect the sample holding chamber 123 with the temperature-controlled chamber 124 (see FIG. 3). The connection cut-off means 170 and 171 are disposed on the respective sides (i.e., both sides) of the sample holding plate 120 at roughly the same height as that of the sample holding plate 120. The connection cut-off means 170 and 171 can open/close the first and second vents 125 and 126, respectively. For example, an open/close shutter that rotates around the valve shaft of the valve body by 90 degrees, such as a butterfly valve, may be used for each of the connection cut-off means 170 and 171. As for the valve body, a plate member made of non-air-permeable material that hardly lets a gas pass through the plate member is preferably used. FIG. 3 shows a state where the open/close shutters are opened. As shown in FIG. 3, when the connection cut-off means 170 and 171 are both opened, wind from the blower means 160 circulates inside the housing 110 by passing through the temperature-controlled chamber 124, the first vent 125, the sample holding chamber 123, the second vent 126, and the temperature-controlled chamber 124 in this listed order. On the other hand, when the connection cut-off means 170 and 171 are closed, even if the blower means 160 sends a wind, this wind from the blower means 160 just flows into the temperature-controlled chamber 124 but comes into direct contact with neither the inside of the sample holding chamber 123 nor the sample SA as shown in FIG. 2.

Next, the control apparatus 102 is explained.

As shown in FIG. 4, the control apparatus 102 includes an operation unit 190, a control unit 180, and a display unit 191.

The operation unit 190 is an input device such as a keyboard and a mouse. The operation unit 190 receives input entered by a user. Examples of commands that a user should enter include a target temperature, a threshold, and a permissible range. Note that the target temperature is a sample temperature that should be attained by the temperature control. Further, the threshold is a value(s) necessary for the operation of the connection cut-off means 170 and 171 and is a temperature(s) close to the target temperature. Further, the permissible range is a range that is used to check whether the sample temperature has entered a steady state or not, and is a predetermined range including the target temperature.

The control unit 180 includes a memory 181, a CPU 182, a blowing connection cut-off controller 183, and a temperature change controller 184.

The CPU 182 controls the temperature changing means 150 and the connection cut-off means 170 and 171 through the blowing connection cut-off controller 183 and the temperature change controller 184, respectively. Further, the CPU 182 controls the display unit 191. The memory 181 stores data necessary for the temperature control received from the CPU 182. The blowing connection cut-off controller 183 controls the connection cut-off means 170 and 171 based on a signal received from the CPU 182 and a signal indicating a sample temperature received from the sample temperature measurement unit 130. The temperature change controller 184 receives a signal indicating a temperature-controlled chamber temperature from the temperature-controlled chamber temperature measurement unit 140, and controls the temperature changing means 150 based on the received temperature-controlled chamber temperature.

The display unit 191 receives a display signal from the control unit 180 and displays information for controlling the temperature of the temperature-controlled bath 101. Examples of display devices used for the display unit 191 include a liquid crystal display device and an organic EL (Electro Luminescence) display device. Note that a touch panel display device may be used for both the operation unit 190 and the display unit 191. Examples of the above-described information items include a sample temperature, a temperature-controlled chamber temperature, a target temperature, a threshold, and a permissible range.

(Temperature Control Method)

Figure 5:
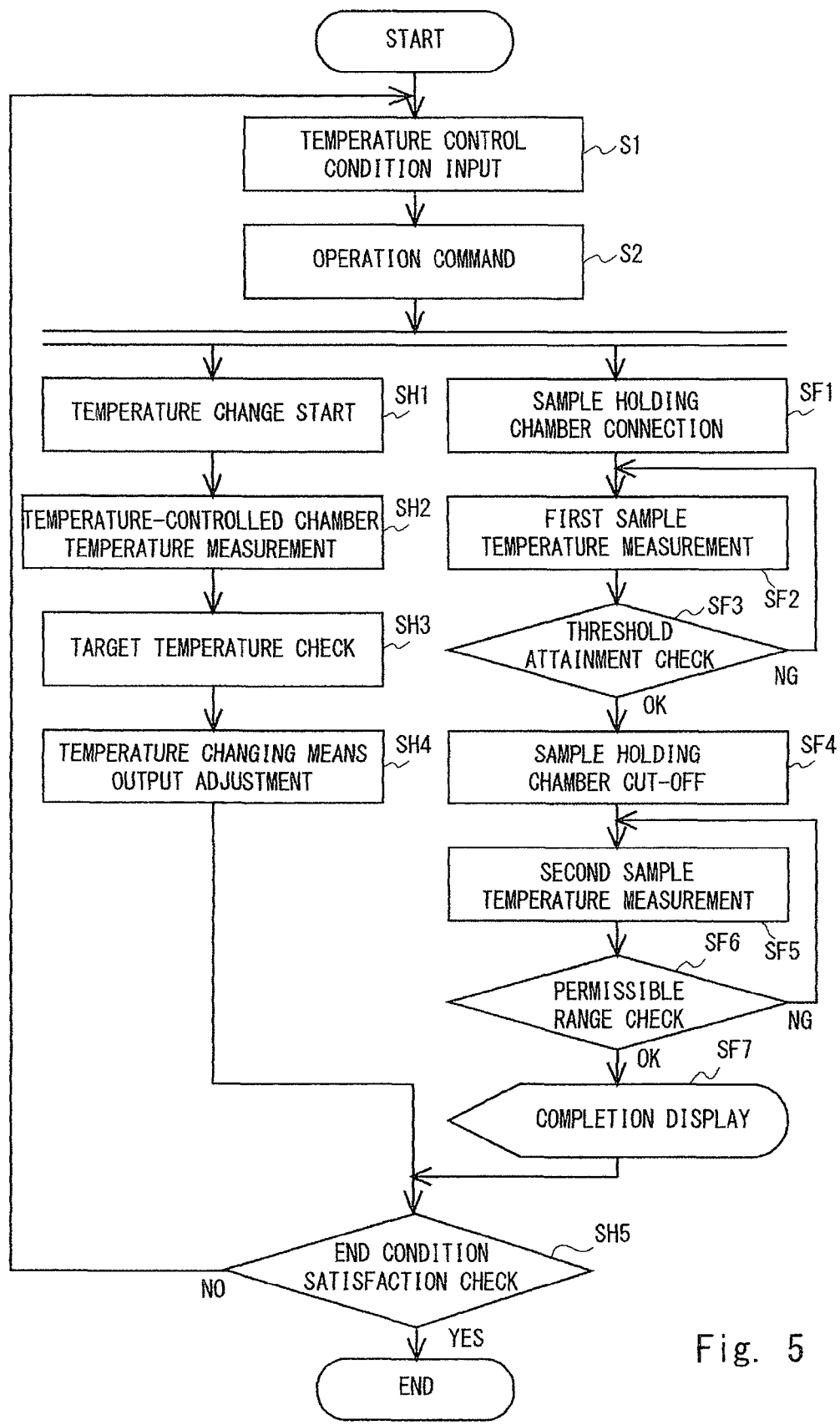
FIG. 5 shows a flowchart of a temperature control method for a temperature-controlled bath system according to the first exemplary embodiment.
Figure 6:
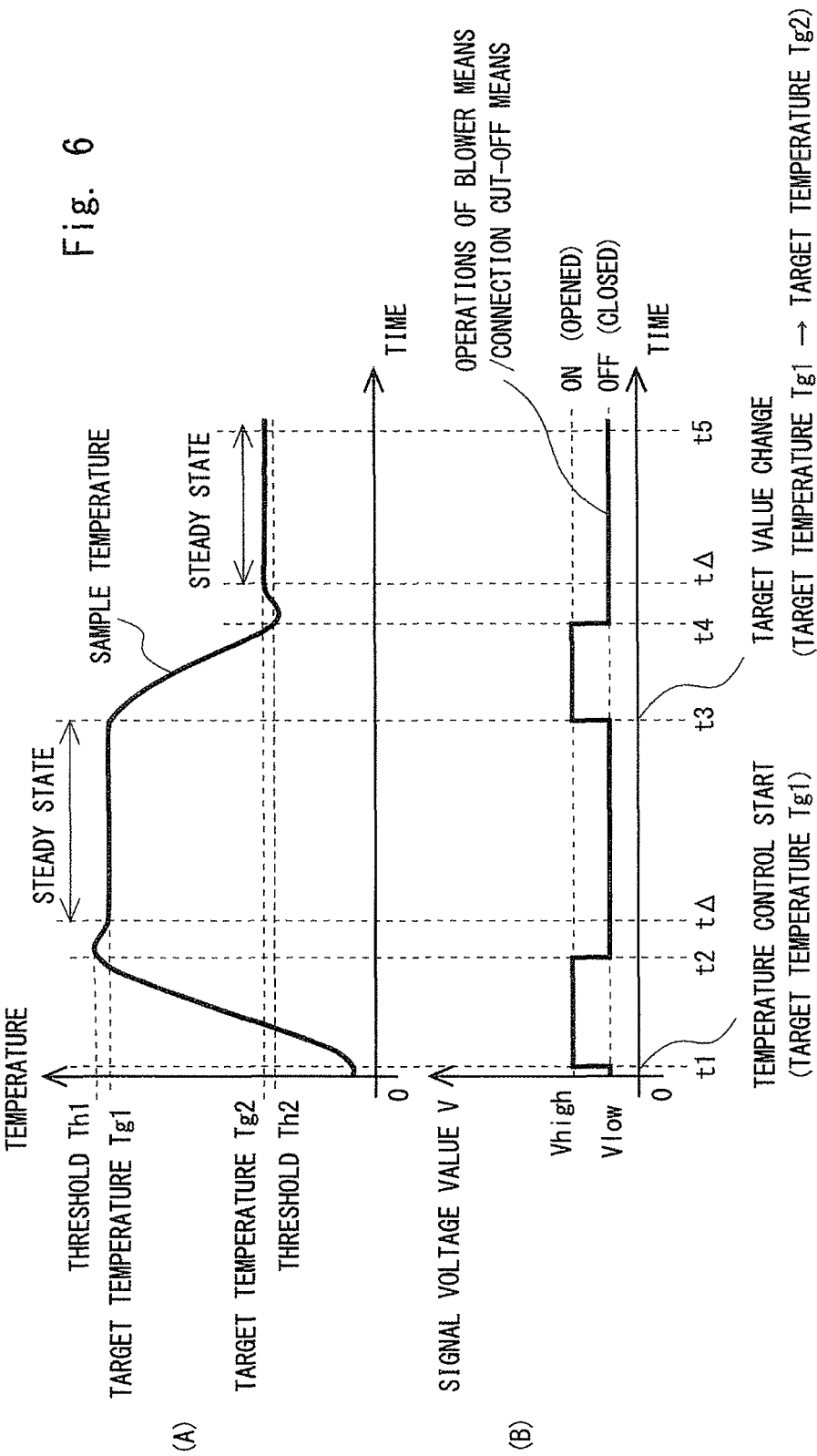
FIG. 6 shows a relation between changes in a sample temperature over time and shutter actions.

Next, a temperature control method is explained with reference to FIGS. 5 and 6. FIG. 5 shows a flowchart of a temperature control method for the temperature-controlled bath system according to the first exemplary embodiment. FIG. 6 shows a relation between changes in the sample temperature over time and shutter actions.

Firstly, when a user enters a command, the operation unit 190 receives an input of information about a condition for performing temperature control (Temperature control condition input step S1). Assume that the user wants to change the sample temperature to a target temperature Tg1 higher than the current sample temperature. The temperature control starts (Operation command step S2). Next, the control of the temperature changing means 150 performed by the temperature change controller 184 and the control of the connection cut-off means 170 and 171 performed by the blowing connection cut-off controller 183 are performed in parallel.

Firstly, the control of the temperature changing means 150 performed by the temperature change controller 184 (SH1 to SH4) is explained. An operation command is provided from the CPU 182 to the temperature change controller 184. As a result, the temperature change controller 184 operates a heat exchanger, which serves as the temperature changing means 150, and thereby starts changing the temperature (Temperature change start step SH1). The blower means 160 starts sending air as the temperature changing means 150 starts operating. Next, the temperature-controlled chamber temperature is measured (Temperature-controlled chamber temperature measurement step SH2). A difference between the temperature-controlled chamber temperature and the target temperature is calculated (Target temperature check step SH3). The output of the heat exchanger is adjusted based on the difference between the temperature-controlled chamber temperature and the target temperature so that the temperature-controlled chamber temperature becomes closer to the target temperature (Temperature changing means output adjustment step SH4).

Next, the control of the connection cut-off means 170 and 171 performed by the blowing connection cut-off controller 183 (SF1 to SF7) is explained with reference to FIGS. 2, 3, 5 and 6.

An operation command is provided from the CPU 182 to the blowing connection cut-off controller 183. As a result, the blowing connection cut-off controller 183 opens the first and second vents 125 and 126 by sending a control signal(s) to the connection cut-off means 170 and 171, respectively (Sample holding chamber connection step SF1). Specifically, as shown in FIG. 6(B), the signal voltage value of the control signal is raised to a voltage Vhigh at a time t1. Assume that the voltage Vhigh indicates an opened state. At this point, as shown in FIG. 3, open/close shutters, which serve as the connection cut-off means 170 and 171, open. As a result, the sample holding chamber 123 is connected with the temperature-controlled chamber 124. The blower means 160 continues sending air while the temperature changing means 150 changes the temperature of the gas (i.e., air). As a result, the gas circulates through the temperature-controlled chamber 124 and the sample holding chamber 123. In this process, the gas, whose temperature has been changed, comes into direct contact with the sample SA and thereby provides heat to the sample SA. As shown in FIG. 6(A), in a period from the time t1 to t2, the temperature of the sample SA quickly changes toward the target temperature Tg1.

The blowing connection cut-off controller 183 measures the sample temperature through the sample temperature measurement unit 130 (First sample temperature measurement step SF2) and checks whether the sample temperature has reached a threshold Th1 or not (Threshold attainment checking step SF3). When the sample temperature is equal to or greater than the threshold Th1 (Threshold attainment checking step SF3: OK), the sample temperature has reached the target temperature. Therefore, the quick temperature change by the direct blowing is not necessary any longer. Therefore, the sample holding chamber 123 is cut off from the temperature-controlled chamber 124 by the connection cut-off means 170 and 171 (Sample holding chamber cut-off step SF4) (see FIG. 2). After that, the heat of the temperature-controlled chamber 124 is slowly transmitted to the gas and the sample SA in the sample holding chamber 123 through the sample holding plate 120 and the sample holding pedestal 122. The temperature of the sample SA is suppressed fluctuating from the target temperature and hence kept at the fixed temperature (t2 to t3).

Then, it is determined whether the sample temperature is stable at the target temperature Tg1. That is, the sample temperature is measured (Second sample temperature measurement step SF5). It is checked whether the sample temperature is continuously kept within a permissible range R1 for a predetermined time period (Permissible range checking step SF6). When the sample temperature is continuously kept within the permissible range R1 (Permissible range checking step SF6: OK), the completion of the temperature change/stabilization is displayed in the display unit 191 (Completion displaying step SF7). Finally, it is checked whether the temperature control end condition is satisfied (End condition satisfaction checking step SH5) and the temperature control is finished.

As described above, the control of the temperature changing means 150 and the control of the connection cut-off means 170 and 171 are performed in parallel.

Note that although the temperature of the sample SA is raised in the above-explained example (t1 to t3), the temperature control method may also be performed in a similar fashion when the temperature of the sample SA is lowered. That is, the target temperature is reset to a target temperature Tg2 and the threshold is reset to a threshold Th2, and then the above-described steps (S1, S2, SH1-SH5, and SF1-SF7) are performed again. As a result, as shown in a period from the time t3 to t5 in FIG. 6, the temperature of the sample SA is changed to the target temperature Tg2 in the time t3 to t4 and brought into a steady state in the time t4 to t5. That is, the sample temperature does not fluctuate from the target temperature Tg2 and is kept at the fixed temperature.

As explained above, according to this exemplary embodiment, the blower means 160 sends air while the temperature changing means 150 changes the temperature of the gas (i.e., air) in the state where the sample holding chamber 123 is connected with the temperature-controlled chamber 124. By doing so, the gas, whose temperature has been changed, comes into direct contact with the sample SA. As a result, the temperature of the sample SA can be swiftly changed to the target temperature Tg1. Further, after the temperature of the sample SA is changed to the target temperature Tg1, the temperature changing means 150 keeps the temperature of the temperature-controlled chamber 124 at the fixed temperature in the state where the sample holding chamber 123 is cut off from the temperature-controlled chamber 124 (which is also referred to as "cut-off state"). As a result, the heat of the gas in the temperature-controlled chamber 124 is slowly transmitted to the gas and the sample SA in the sample holding chamber 123 through the sample holding plate 120 and the sample holding pedestal 122. In this way, the temperature of the sample SA is suppressed fluctuating from the target temperature and hence is kept at the fixed temperature.

Further, the temperature-controlled bath system 100 according to the first exemplary embodiment may be disposed inside a linear expansion coefficient measuring device (not shown) and used in that state. This linear expansion coefficient measuring device can swiftly change the temperature of the sample SA to the target temperature, and after the temperature change, keep the temperature of the sample SA at the fixed temperature. Therefore, the linear expansion coefficient measuring device can accurately measure the coefficient of linear expansion of the sample SA in a short time.

Further, in this exemplary embodiment, the sample holding plate 120 is made of thermally conductive material. Therefore, after the temperature of the sample SA is changed to the target temperature Tg1, the temperature of the sample SA can be further suppressed fluctuating and hence settled in a short time. Further, when the sample holding plate 120 includes a radiator plate, the temperature of the sample SA can be settled in a shorter time.

Further, since the housing 110 is made of insulating material, the temperature-controlled chamber 124 and the sample holding chamber 123 are hardly affected by the external heat. Further, since the housing 110 prevents heat from escaping to the outside, the temperature of the sample SA is changed to the target temperature and kept at the fixed temperature in a more stable fashion.

Second Exemplary Embodiment

Figure 7:
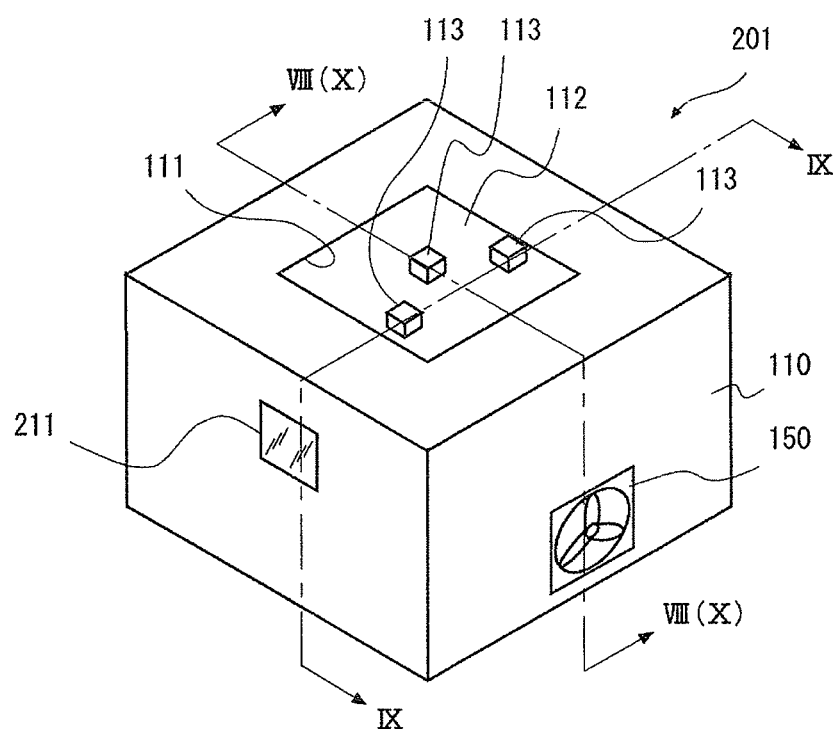
FIG. 7 is a perspective view of a temperature-controlled bath according to a second exemplary embodiment.
Figure 8:
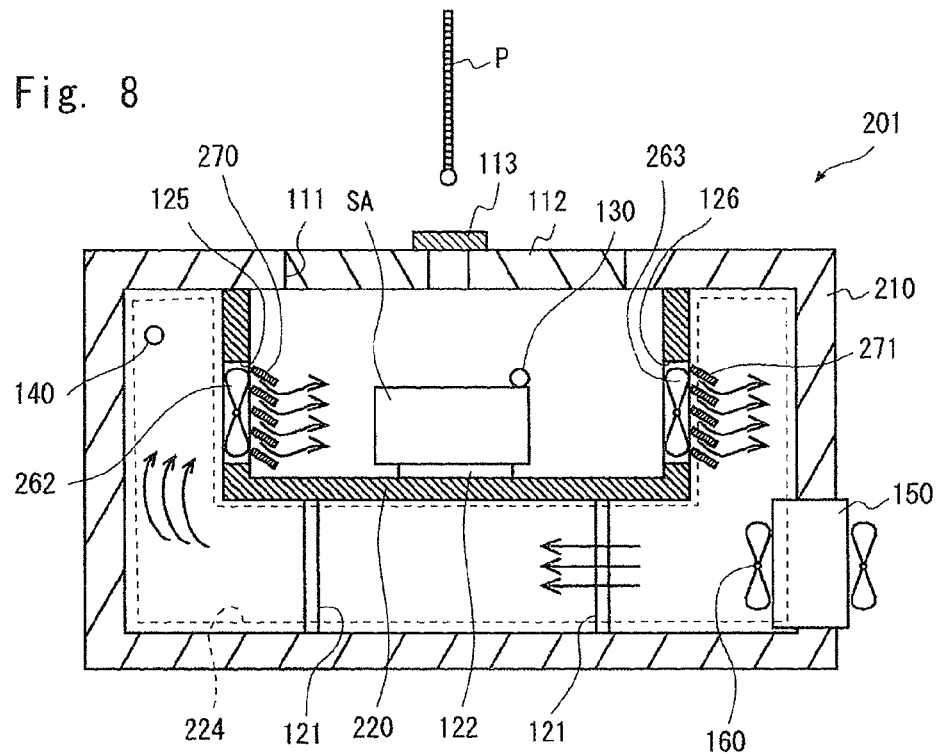
FIG. 8 is a sectional front view of a temperature-controlled bath according to the second exemplary embodiment.
Figure 9:
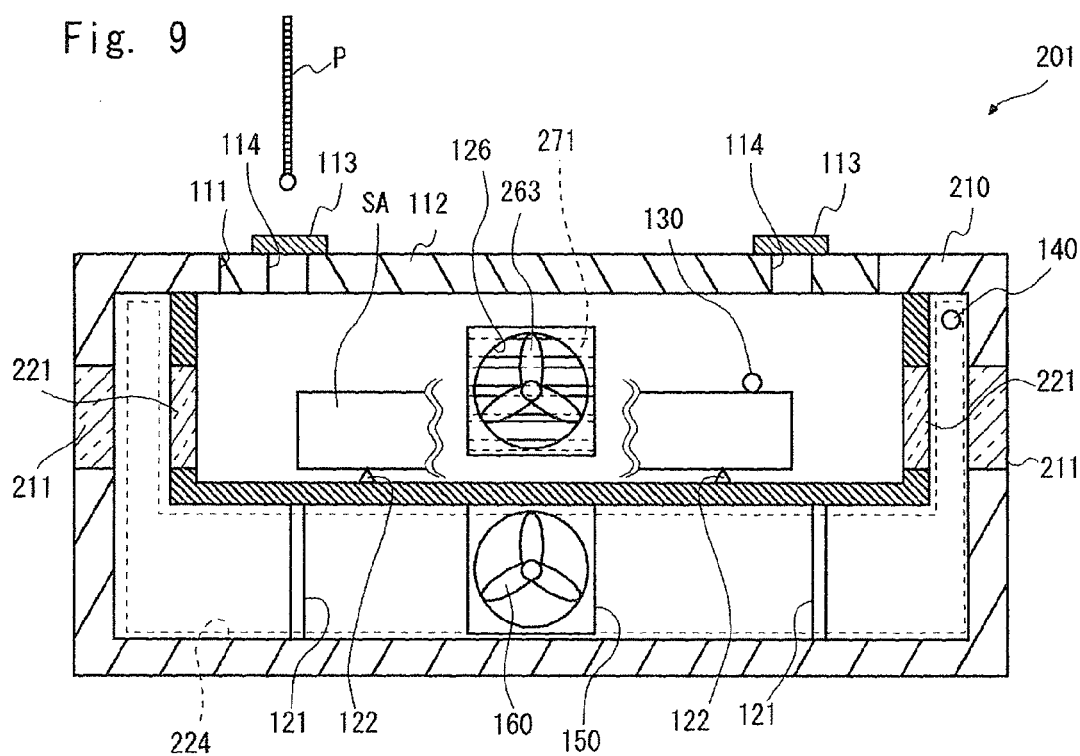
FIG. 9 is a sectional side view of a temperature-controlled bath according to the second exemplary embodiment.
Figure 10:
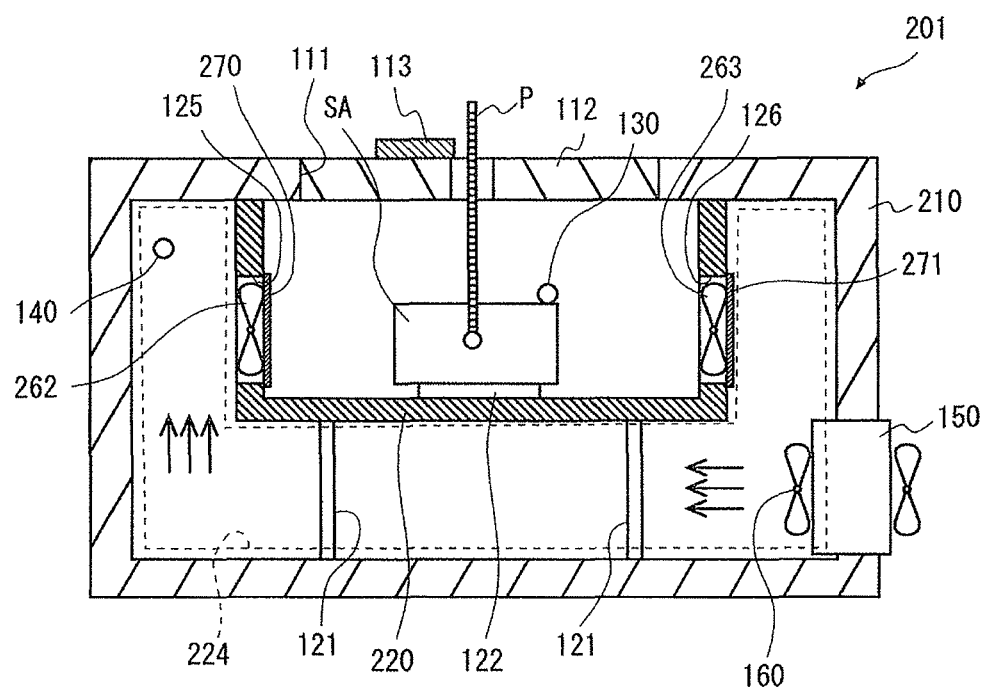
FIG. 10 is a sectional front view of a temperature-controlled bath according to the second exemplary embodiment.
Figure 11:
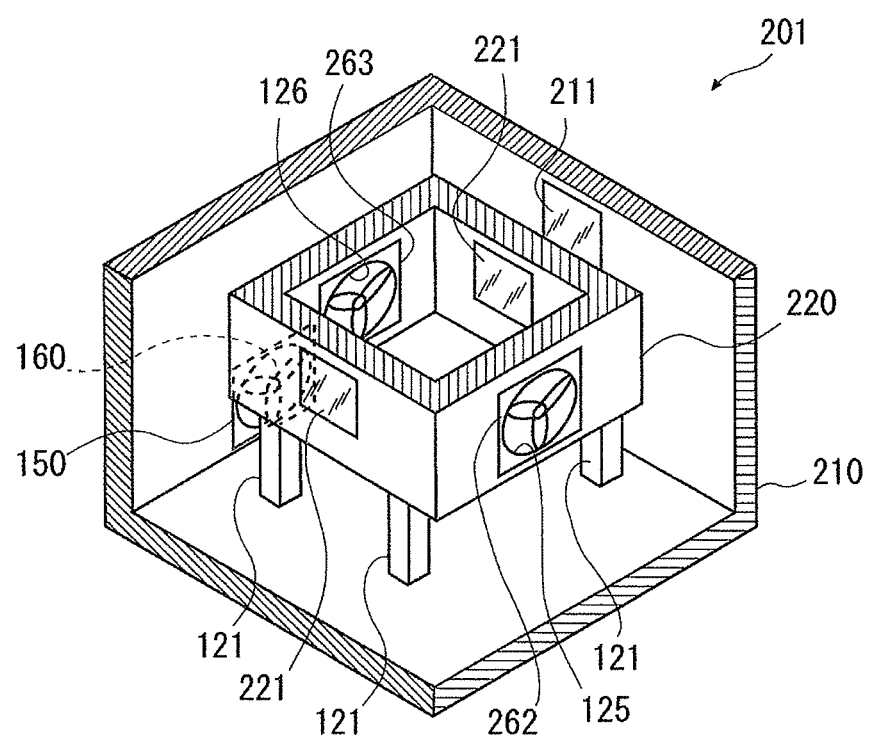
FIG. 11 shows the internal space of a temperature-controlled bath according to the second exemplary embodiment.

Next, a temperature-controlled bath according to a second exemplary embodiment is explained with reference to FIGS. 7 to 11. FIG. 7 is a perspective view of the temperature-controlled bath according to the second exemplary embodiment. FIGS. 8 and 10 show a sectional front view of the temperature-controlled bath according to the second exemplary embodiment. FIG. 9 is a sectional side view of the temperature-controlled bath according to the second exemplary embodiment. FIG. 11 shows the internal space of the temperature-controlled bath according to the second exemplary embodiment. The temperature-controlled bath according to the second exemplary embodiment is similar to the temperature-controlled bath 101 according to the first exemplary embodiment except for the housing, the sample holding chamber, and the blower means. The other elements of the configuration are the same as those of the temperature-controlled bath 101, and therefore the same symbols as those used in the first exemplary embodiment are used in the following explanation.

As shown in FIGS. 7, 8, 9 and 11, the temperature-controlled bath 201 includes a housing 210 and a sample holding chamber 220. Similarly to the temperature-controlled bath 101, the temperature-controlled bath 201 is controlled by a control apparatus (not shown). Similarly to the housing 110, the housing 210 is a roughly rectangular parallelepiped housing made of insulating material. Further, the housing 210 includes an optically transparent window 211 in the sidewall. The position and/or the material of the optically transparent window 211 may be changed as desired to facilitate optical measurement of the sample SA. The housing 210 includes a space around the sample holding chamber 220. This space serves as a temperature-controlled chamber 224.

The sample holding chamber 220 is supported by supporting legs 121 and disposed inside the housing 210. In the sample holding chamber 220, a first vent 125 and a second vent 126 are formed. Similarly to the sample holding plate 120, the sample holding chamber 220 is made of thermally conductive material having a high thermal conductivity. The sample holding chamber 220 preferably has a predetermined wall thickness so that the sample holding chamber 220 slowly (or gently) conducts heat from the temperature-controlled chamber 224 to the sample SA. Further, the sample holding chamber 220 includes an optically transparent window 221 in the sidewall. Similarly to the optically transparent window 211, the position and/or the material of the optically transparent window 221 may be changed as desired to facilitate optical measurement of the sample SA. By using optical measurement means (which is also referred to as "measurement means"), it is possible to measure the length of the sample SA through the optically transparent windows 211 and 221 without opening the lid.

The blower means 160 does not have to have sufficient blowing ability to circulate the gas inside the housing 210. That is, the blower means 160 just needs to have at least a sufficient blowing ability to stir the gas in the temperature-controlled chamber 224. The blowing direction of the blower means 160 is a direction toward the temperature-controlled chamber 224.

Second blower means 262 is disposed in the first vent 125 and sends air so that the gas (i.e., air) in the temperature-controlled chamber 224 flows into the sample holding chamber 220. After the gas in the temperature-controlled chamber 224 flows into the sample holding chamber 220, the gas comes into contact with the sample SA. Further, third blower means 263 is disposed in the second vent 126 and sends air so that the gas (i.e., air) in the sample holding chamber 220 flows out toward the temperature-controlled chamber 224. Each of the second and third blower means 262 and 263 starts or stops sending air in response to a reception of a control signal.

Connection cut-off means 270 and 271 are disposed in the sidewall of the sample holding chamber 220, and can cut off the sample holding chamber 220 from the temperature-controlled chamber 224 (see FIG. 10) or connect the sample holding chamber 220 with the temperature-controlled chamber 224 (see FIG. 8). In this embodiment, a blind-type shutter, for example, is used for each of the connection cut-off means 270 and 271. The blind-type shutter can open/close in a smaller space than that for the open/close shutter. FIG. 8 shows a state where the blind-type shutters are opened. As shown in FIG. 8, when the connection cut-off means 270 and 271 are both opened, a wind from the blower means 160 flows into the temperature-controlled chamber 224. Next, a wind from the second blower means 262 flows into the sample holding chamber 220 through the first vent 125. Finally, a wind from the third blower means 263 flows into the temperature-controlled chamber 224 through the second vent 126. In this way, the wind from the blower means 160 circulates inside the housing 210 by passing through the temperature-controlled chamber 224, the first vent 125, the sample holding chamber 220, the second vent 126, and the temperature-controlled chamber 224 in this listed order. On the other hand, when the connection cut-off means 270 and 271 are closed, even if the blower means 160 sends a wind, this wind from the blower means 160 just flows into the temperature-controlled chamber 224 but comes into direct contact with neither the inside the sample holding chamber 220 nor the sample SA as shown in FIG. 10.

Next, a control apparatus 202 (not shown) for the temperature-controlled bath 201 is explained. The control apparatus 202 is similar to the control apparatus 102 except for the blowing connection cut-off controller. A blowing connection cut-off controller 283 (not shown) for the temperature-controlled bath 201 controls the second and third blower means 262 and 263 in addition to the connection cut-off means 270 and 271.

Next, a temperature control method according to the second exemplary embodiment is explained. The temperature control method according to the second exemplary embodiment is similar to the temperature control method according to the first exemplary embodiment except for the sample holding chamber connection step SF1 and the sample holding chamber cut-off step SF4. Therefore, only the sample holding chamber connection step SF1 and the sample holding chamber cut-off step SF4 are explained.

In the sample holding chamber connection step SF1, as shown in FIG. 8, the blower means 160 sends air and the connection cut-off means 270 and 271 connect the sample holding chamber 220 with the temperature-controlled chamber 224. Further, the second and third blower means 262 and 263 start sending air.

In the sample holding chamber cut-off step SF4, as shown in FIG. 10, the connection cut-off means 270 and 271 cut off the sample holding chamber 220 from the temperature-controlled chamber 224 and the second and third blower means 262 and 263 stop sending air.

As explained above, according to the temperature-controlled bath 201 in accordance with the second exemplary embodiment, similarly to the above-described first exemplary embodiment, the blower means 160 and the second and third blower means 262 and 263 send air while the temperature changing means 150 changes the temperature of the gas (i.e., air) in the state where the sample holding chamber 220 is connected with the temperature-controlled chamber 224. By doing so, the gas, whose temperature has been changed, comes into direct contact with the sample SA. As a result, the temperature of the sample SA can be swiftly changed to the target temperature Tg1. Further, after the temperature of the sample SA is changed to the target temperature Tg1, the temperature changing means 150 keeps the temperature of the temperature-controlled chamber 224 at the fixed temperature in the state where the sample holding chamber 220 is cut off from the temperature-controlled chamber 224 (which is also referred to as "cut-off state"). As a result, the heat of the gas in the temperature-controlled chamber 224 is slowly transmitted to the gas and the sample SA in the sample holding chamber 220 through the sample holding chamber 220 and the sample holding pedestal 122. In this way, the temperature of the sample SA is suppressed fluctuating from the target temperature and hence is kept at the fixed temperature.

Further, similarly to the above-described first exemplary embodiment, the temperature-controlled bath 201 according to the second exemplary embodiment may be disposed inside a linear expansion coefficient measuring device together with the control apparatus (not shown) and used in that state. Similarly to the above-described first exemplary embodiment, the linear expansion coefficient measuring device can measure the length of the sample SA at a plurality of temperatures by using the probe P and thereby measures the coefficient of linear expansion of the sample SA.

Further, in the temperature-controlled bath 201 according to the second exemplary embodiment, the blower means 160 does not have to have sufficient blowing ability to circulate the gas, provided that the blower means 160 and the second and third blower means 262 and 263 collectively have sufficient blowing ability to circulate the gas. Therefore, the blower means 160 according to the second exemplary embodiment may have a smaller blowing ability compared to that of the blower means 160 according to the first exemplary embodiment. Further, when the blower means 160 according to the second exemplary embodiment has the same blowing ability as that of the blower means 160 according to the first exemplary embodiment, the housing 210 may have a larger size that that of the housing 110 according to the first exemplary embodiment. That is, the temperature-controlled bath 201 can be used for a wider variety of shapes and sizes of samples than those for the temperature-controlled bath 101.

Note that although the third blower means 263 is provided in the second vent 126 in the second exemplary embodiment, the third blower means 263 may be omitted when the blower means 160 and the second blower means 262 collectively have sufficient blowing ability to circulate the gas.

Third Exemplary Embodiment

Figure 12:
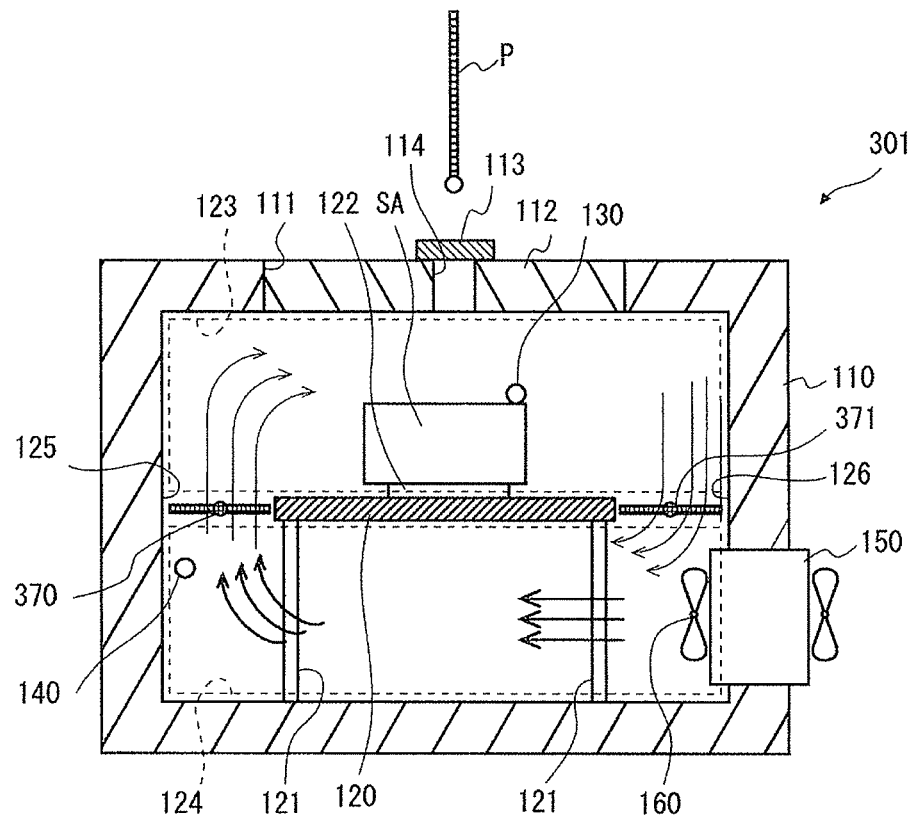
FIG. 12 is a cross section of a temperature-controlled bath according to a third exemplary embodiment.
Figure 13:
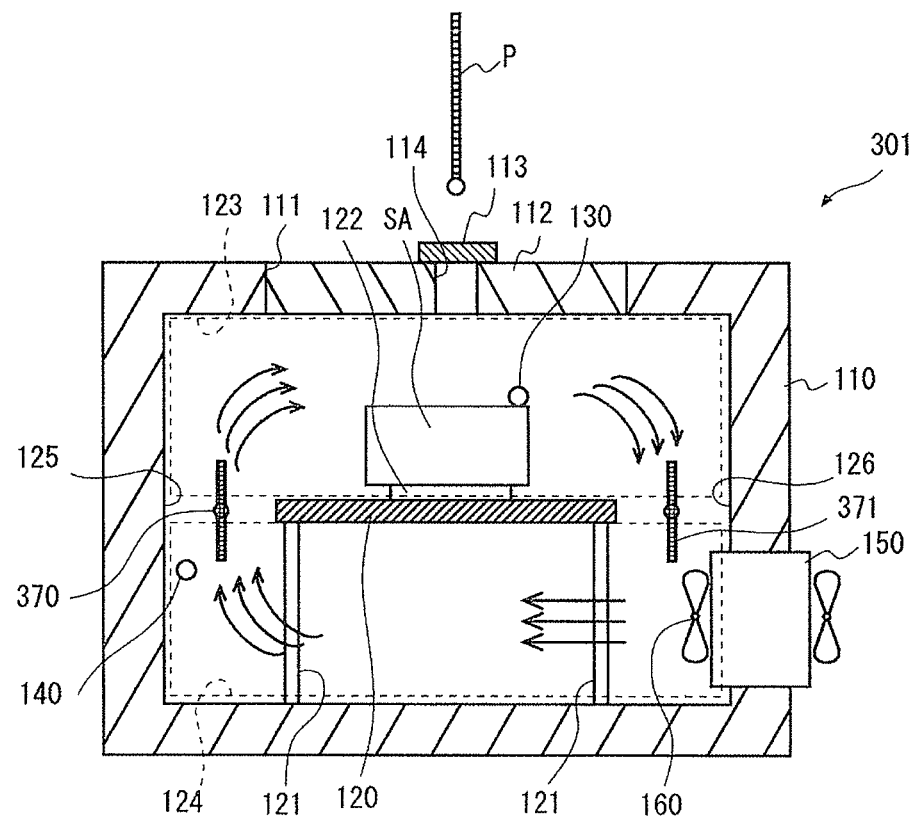
FIG. 13 is a cross section of a temperature-controlled bath according to the third exemplary embodiment.

Next, a temperature-controlled bath according to a third exemplary embodiment is explained with reference to FIGS. 12 and 13. FIGS. 12 and 13 show cross sections of the temperature-controlled bath according to the third exemplary embodiment. The temperature-controlled bath according to the third exemplary embodiment is similar to the temperature-controlled bath 101 according to the first exemplary embodiment except for the connection cut-off means. The other elements of the configuration are the same as those of the temperature-controlled bath 101, and therefore the same symbols as those used in the first exemplary embodiment are used in the following explanation.

As shown in FIG. 12, the temperature-controlled bath 301 includes connection cut-off means 370 and 371. Similarly to the connection cut-off means 170 and 171, the connection cut-off means 370 and 371 are disposed between the sample holding plate 120 and the housing 110. The connection cut-off means 370 and 371 can cut off the sample holding chamber 123 from the temperature-controlled chamber 124 (see FIG. 12) or connect the sample holding chamber 123 with the temperature-controlled chamber 124 (see FIG. 13). Further, the connection cut-off means 370 and 371 are disposed on the respective sides (i.e., both sides) of the sample holding plate 120 at roughly the same height as that of the sample holding plate 120. The connection cut-off means 370 and 371 can open/close the first and second vents 125 and 126, respectively. An open/close shutter that rotates around the valve shaft of the valve body by 90 degrees, such as a butterfly valve, is used for each of the connection cut-off means 370 and 371. As for the valve body, an air-permeable plate member that can let a gas pass through the plate member is used. Examples of the air-permeable plate member include a plate member composed of punching metal, a plate member composed of wire netting, a perforated plate with a number of small holes formed therein, and a plate member made of porous material. FIG. 13 shows a state where the open/close shutters are opened. As shown in FIG. 13, similarly to the temperature-controlled bath 101, when the connection cut-off means 370 and 371 are both opened, wind from the blower means 160 circulates inside the housing 110 by passing through the temperature-controlled chamber 124, the first vent 125, the sample holding chamber 123, the second vent 126, and the temperature-controlled chamber 124 in this listed order. On the other hand, when the connection cut-off means 370 and 371 are closed and the blower means 160 sends a wind as shown in FIG. 12, a part of this wind flows into the temperature-controlled chamber 124. Meanwhile, the remaining part of the wind from the blower means 160 passes through the connection cut-off means 370 and comes into direct contact with the inside of the sample holding chamber 123 and the sample SA.

As explained above, according to the temperature-controlled bath 301 in accordance with the third exemplary embodiment, similarly to the temperature-controlled bath 101, the blower means 160 sends air while the temperature changing means 150 changes the temperature of the gas (i.e., air) in the state where the sample holding chamber 123 is connected with the temperature-controlled chamber 124. By doing so, the gas, whose temperature has been changed, comes into direct contact with the sample SA. As a result, the temperature of the sample SA can be swiftly changed to the target temperature Tg1. Further, after the temperature of the sample SA is changed to the target temperature Tg1, the temperature changing means 150 keeps the temperature of the temperature-controlled chamber 124 at the fixed temperature in the state where the sample holding chamber 123 is cut off from the temperature-controlled chamber 124 (which is also referred to as "cut-off state"). As a result, the heat of the gas in the temperature-controlled chamber 124 is slowly transmitted to the gas and the sample SA in the sample holding chamber 123 through the sample holding plate 120 and the sample holding pedestal 122. Further, since the blower means 160 sends air while the temperature changing means 150 changes the temperature of the gas (i.e., air), part of the gas comes into direct contact with the sample SA. As a result, the amount of the gas flowing into the sample holding chamber 123 is reduced and hence the amount of the wind coming into direct contact with the sample SA is reduced. Therefore, the temperature of the sample SA is suppressed fluctuating from the target temperature and hence is kept at the fixed temperature. That is, the stable temperature control can be achieved by appropriately adjusting the amount of the gas flowing into the sample holding chamber 123.

Further, although the temperature changing means 150 is controlled based on the sample temperature in the first and second exemplary embodiments, the temperature changing means 150 may be controlled based on the temperature-controlled chamber temperature. Further, although the open/close shutters are used as the connection cut-off means 170 and 171 in the first exemplary embodiment, blind-type shutters may be used as the connection cut-off means 170 and 171. Further, although the blind-type shutters are used as the connection cut-off means 270 and 271 in the second exemplary embodiment, open/close shutters may be used as the connection cut-off means 270 and 271. In consideration of the wind circulation, two air holes, i.e., first and second vents 125 and 126 are preferably provided. However, the only requirement is that the gas should flow into and flow out through the air hole(s). Therefore, only one of the first and second vents 125 and 126 may be provided.

Further, although the temperature changing means 150 heats or cools the gas in the temperature-controlled chamber 124 and thereby changes its temperature to a predetermined temperature in the first and second exemplary embodiments, the temperature changing means 150 may heat or cool the housing 110 itself and thereby change the temperature of the temperature-controlled chamber 124. When the temperature changing means 150 heats or cools the housing 110 itself as described above, a housing having a double structure composed of a roughly rectangular parallelepiped inner housing and a roughly rectangular parallelepiped outer housing enclosing the inner housing, for example, may be used as the housing 110. Specifically, the inner housing is made of thermally conductive material and the outer housing is Made of insulating material. Further, as for the temperature changing means 150, a Peltier element, for example, may be used. The Peltier element is disposed in the inner housing. Further the Peltier element is connected to a power supply located outside the temperature-controlled bath 101 and supplied with an electric current from the power supply. With this configuration, the Peltier element heats or cools the inner housing and thereby heats or cools the housing 110 itself. By doing so, the Peltier element can change the temperature of the temperature-controlled chamber 124.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A temperature-controlled bath comprising:
   temperature changing means for heating or cooling a gas so that the temperature of the gas is adjusted to a set temperature;
   a temperature-controlled chamber whose temperature is adjusted by the temperature changing means, the temperature changing means being disposed in the temperature-controlled chamber;
   a sample holding chamber containing a sample therein, the sample holding chamber being separated from the temperature-controlled chamber by a thermally conductive wall;
   and connection cut-off means for changing a connection between the temperature-controlled chamber and the sample holding chamber to a connected state or a cut-off state.

2. The temperature-controlled bath according to claim 1, further comprising first blower means for sending a gas whose temperature is adjusted by the temperature changing means mainly into the temperature-controlled chamber.

3. The temperature-controlled bath according to claim 1, further comprising
   an air hole that serves as an inlet/outlet of the gas between the temperature-controlled chamber and the sample holding chamber;
   second blower means for sending the gas in the temperature-controlled chamber into the sample holding chamber through the air hole; and
   third blower means for sending out the gas in the sample holding chamber toward the temperature-controlled chamber through the air hole.

4. The temperature-controlled bath according to claim 1, wherein the thermally conductive wall comprises at least one of a radiator plate protruding toward the temperature-controlled chamber and a radiator plate protruding toward the sample holding chamber.

5. The temperature-controlled bath according to claim 1, wherein the sample holding chamber comprises a probe inserting hole for inserting a probe into the sample holding chamber, the probe inserting hole being able to be opened and closed.

6. The temperature-controlled bath according to claim 1, wherein the sample holding chamber comprises an optically transparent window for enabling optical measurement of the sample.

7. The temperature-controlled bath according to claim 1, wherein
   the connection cut-off means is an open/close shutter that opens/closes by rotating a plate member, and
   the plate member is an air-permeable plate member capable of letting a gas pass through the plate member.

8. A linear expansion coefficient measuring device comprising:
   a temperature-controlled bath;
   measurement means for measuring a length of the sample at different temperatures; and calculation means for calculating a coefficient of linear expansion of the sample based on the length of the sample at each temperature, wherein
   the temperature-controlled bath comprises:
   temperature changing means for heating or cooling a gas so that the temperature of the gas is adjusted to a set temperature;
   a temperature-controlled chamber whose temperature is adjusted by the temperature changing means, the temperature changing means being disposed in the temperature-controlled chamber;
   a sample holding chamber containing a sample therein, the sample holding chamber being separated from the temperature-controlled chamber by a thermally conductive wall; and
   connection cut-off means for changing a connection between the temperature-controlled chamber and the sample holding chamber to a connected state or a cut-off state.

9. A temperature-controlled bath comprising:
a temperature changing unit that heats or cools a gas so that the temperature of the gas is adjusted to a set temperature;
a temperature-controlled chamber whose temperature is adjusted by the temperature changing unit, the temperature changing unit being disposed in the temperature-controlled chamber;
a sample holding chamber containing a sample therein, the sample holding chamber being separated from the temperature-controlled chamber by a thermally conductive wall; and
a connection cut-off unit that changes a connection between the temperature-controlled chamber and the sample holding chamber to a connected state or a cut-off state.

10. The temperature-controlled bath according to claim 9, further comprising a first blower unit that sends a gas whose temperature is adjusted by the temperature changing unit mainly into the temperature-controlled chamber.

11. The temperature-controlled bath according to claim 9, further comprising
an air hole that serves as an inlet/outlet of the gas between the temperature-controlled chamber and the sample holding chamber;
a second blower unit that sends the gas in the temperature-controlled chamber into the sample holding chamber through the air hole; and
a third blower unit that sends out the gas in the sample holding chamber toward the temperature-controlled chamber through the air hole.

12. The temperature-controlled bath according to claim 9, wherein
the connection cut-off unit is an open/close shutter that opens/closes by rotating a plate member, and
the plate member is an air-permeable plate member capable of letting a gas pass through the plate member.

* * * * *

UNITED STATES PATENT AND TRADEMARK OFFICE
CERTIFICATE OF CORRECTION

PATENT NO. : 9,518,944 B2
APPLICATION NO. : 14/295781
DATED : December 13, 2016
INVENTOR(S) : Y. Yokoyama et al.

Page 1 of 1

It is certified that error appears in the above-identified patent and that said Letters Patent is hereby corrected as shown below:

On the Title Page

Abstract, Column 2, Line 12, please change "conducive wall" to -- conductive wall --

Signed and Sealed this
Twenty-second Day of May, 2018

Andrei Iancu
*Director of the United States Patent and Trademark Office*